US008323937B2

(12) United States Patent     (10) Patent No.: US 8,323,937 B2
Zhang et al.     (45) Date of Patent: Dec. 4, 2012

(54) CONTINUOUS CATALYTIC GENERATION OF POLYOLS FROM CELLULOSE

(75) Inventors: Tao Zhang, Dalian (CN); Aiqin Wang, Dalian (CN); Mingyuan Zheng, Dalian (CN); Changzhi Li, Dalian (CN); Jifeng Pang, Dalian (CN); Tom N. Kalnes, LaGrange, IL (US); John Q. Chen, Glenview, IL (US); Joseph A. Kocal, Glenview, IL (US)

(73) Assignees: UOP LLC, Des Plaines, IL (US); Dalian Institute of Chemical Physics, Dalian (CN)

( * ) Notice: Subject to any disclaimer, the term of this patent is extended or adjusted under 35 U.S.C. 154(b) by 0 days.

(21) Appl. No.: 13/192,739

(22) Filed: Jul. 28, 2011

(65) Prior Publication Data

US 2011/0312050 A1    Dec. 22, 2011

(51) Int. Cl.
*C12P 7/18* (2006.01)
*C07C 31/20* (2006.01)
(52) U.S. Cl. ........................................ 435/158; 568/861
(58) Field of Classification Search .................. None
See application file for complete search history.

(56) References Cited

U.S. PATENT DOCUMENTS

| | | | |
|---|---|---|---|
| 4,239,633 A | 12/1980 | Gutierrez et al. | |
| 5,227,356 A | 7/1993 | Hess et al. | |
| 5,616,304 A | 4/1997 | Stormo | |
| 6,162,350 A | 12/2000 | Soled et al. | |
| 6,436,279 B1 | 8/2002 | Colyar | |
| 6,447,645 B1 | 9/2002 | Barrett et al. | |
| 6,627,780 B2 | 9/2003 | Wu et al. | |
| 7,767,867 B2 | 8/2010 | Cortright | |
| 7,960,594 B2 * | 6/2011 | Zhang et al. | 568/861 |
| 2004/0175806 A1 | 9/2004 | Werpy et al. | |
| 2009/0130502 A1 | 5/2009 | Liu et al. | |
| 2010/0255983 A1 | 10/2010 | Zhang | |
| 2011/0046419 A1 * | 2/2011 | Zhang et al. | 568/852 |

FOREIGN PATENT DOCUMENTS

| | | |
|---|---|---|
| WO | 2006/092085 A1 | 9/2006 |
| WO | 2010/045766 A1 | 4/2010 |
| WO | 2010/060345 A1 | 6/2010 |
| WO | 2011/113281 A1 | 9/2011 |

OTHER PUBLICATIONS

Luo et al., "Cellulose conversion into polyols catalyzed by reversibly formed acids and supported Ruthenium clusters in hot water", Angew. Chem. Int. Ed. 46: 7636-7639 (2007).*
Fukuoka and Dhepe, "Catalytic conversion of cellulose into sugar alcohols", Angew. Chem. Int. Ed. 45: 5161-5163 (2006).*
Ji, "Catalytic conversion of cellulose into ethylene glycol over supported carbide catalysts", Catalysis Today, 2009, pp. 75-85, vol. 147, Issue 2.
Ji, "Direct Catalytic Conversion of Cellulose into Ethylene Glycol Using Nickel-Promoted Tungsten Carbide Catalysts", Angew. Chem. Int. Ed, 2008, pp. 8510-8513, vol. 47, Issue 44.
Zhang, "A new 3D mesoporous carbon replicated from commercial silica as a catalyst support for direct conversion of cellulose into ethylene glycol", Chem. Commun., 2010, pp. 862-864, vol. 46, Issue 6.
Zhang, "Hydrolysis of cellulose into glucose over carbons sulfonated at elevated temperatures", Chem Commun., 2010, pp. 6935-6937, vol. 46, Issue 37.
Zhang, "Catalytic Hydrogenation of Corn Stalk to Ethylene Glycol and 1,2-Propylene Glycol", Ind. End. Chem, Res., 2011,pp. 6601-6608, vol. 50, Issue 11.
Zhang, "Transition Metal—Tungsten Bimetallic Catalysts for the Conversion of Cellulose into Ethylene Glycol", ChemSusChem, 2010, pp. 63-66, vol. 50, Issue 11.
Jin, "Effect of Ni Promoter on Dibenzothiophene Hydrodesulfurization Performance of Molybdenum Carbide Catalyst", Chinese Jour. of Catalysis, 2006, pp. 899-903, vol. 27, Issue 10.
Narayan, "Ethylene Glycol and Other monomeric Polyols from Biomass", Biotechnology and Bioengineering Symposium, No. 14, 1984, pp. 563-571.
Zhou, "One-pot Conversion of Jerusalem Artichoke Tubers into Polyols", 7th Asia Pacific Conference on Sustainable Energy and Environmental Technologies, Oct. 15-17, 2009.
China Explores in Manufacture of Ethylene Glycol from Renewable Resources', China Petroleum processing and Petrochemical Technology, No. 1, 2009, p. 44.
Zheng, "Direct Catalytic Conversion Cellulose into Ethylene Glycol", 8th World Congress of Chemical Engineering, 2009, p. 512e.
U.S. Office action dated Dec. 14, 2011 for U.S. Appl. No. 13/192,835, Kalnes et al.
U.S. Office action dated Dec. 14, 2011 for U.S. Appl. No. 13/193,200, Kalnes et al.
U.S. Office action dated Dec. 15, 2011 for U.S. Appl. No. 13/193,227, Kalnes et al.
U.S. Office action dated Dec. 9, 2011 for U.S. Appl. No. 13/192,907, Chen et al.
U.S. Office action dated Dec. 14, 2011 for U.S. Appl. No. 13/192,970, Kalnes et al.
U.S. Office action dated Dec. 15, 2011 for U.S. Appl. No. 13/193,007, Chen et al.
U.S. Office action dated Dec. 15, 2011 for U.S. Appl. No. 13/193,072, Kalnes et al.
Applicant's Mar. 14, 2012 response to the Dec. 14, 2011 Office Action for U.S. Appl. No. 13/192,835, Kalnes et al.
Applicant's Mar. 12, 2012 response to the Dec. 14, 2011 Office Action for U.S. Appl. No. 13/193,200, Kalnes et al.
Applicant's Mar. 12, 2012 response to the Dec. 15, 2011 Office Action for U.S. Appl. No. 13/193,227, Kalnes et al.
Applicant's Mar. 9, 2012 response to the Dec. 9, 2011 Office Action for U.S. Appl. No. 13/192,90, Chen et al.

(Continued)

*Primary Examiner* — Anand Desai
(74) *Attorney, Agent, or Firm* — Maryann Maas

(57) ABSTRACT

A catalytic process for generating at least one polyol from a feedstock comprising cellulose is performed in a continuous manner using a catalyst comprising nickel tungsten carbide. The process involves, contacting, continuously, hydrogen, water, and a feedstock comprising cellulose, with the catalyst to generate an effluent stream comprising at least one polyol and recovering the polyol from the effluent stream.

25 Claims, 2 Drawing Sheets

OTHER PUBLICATIONS

Applicant's Mar. 12, 2012 response to the Dec. 14, 2011 Office Action for U.S. Appl. No. 13/192,970, Kalnes et al.
Applicant's Mar. 12, 2012 response to the Dec. 15, 2011 Office Action for U.S. Appl. No. 13/193,007, Chen et al.
Applicant's Mar. 12, 2012 response to the Dec. 15, 2011 Office Action for U.S. Appl. No. 13/193,072, Kalnes et al.
U.S. Office Action dated Apr. 19, 2012 for U.S. Appl. No. 13/192,835, Kalnes et al.
U.S. Office Action dated May 11, 2012 for U.S. Appl. No. 13/192,007, Chen et al.
U.S. Office Action dated May 10, 2012 for U.S. Appl. No. 13/193,007, Chen et al.

* cited by examiner

CONTINUOUS CATALYTIC GENERATION OF POLYOLS FROM CELLULOSE

FIELD OF THE INVENTION

The invention relates to a continuous process for generating at least one polyol from a cellulose containing feedstock. The process involves, contacting, continuously, hydrogen, water, and a feedstock comprising cellulose, with a catalyst to generate an effluent stream comprising at least one polyol and recovering the polyol from the effluent stream. The catalyst consists essentially of at least two active metal components selected from the group consisting of: (i) Mo, W, V, Ni, Co, Fe, Ta, Nb, Ti, Cr, Zr and combinations thereof wherein the metal is in the elemental state or the metal is a carbide compound, a nitride compound, or a phosphide compound; (ii) Pt, Pd, Ru, and combinations thereof wherein the metal is in the elemental state; and (iii) any combination of (i) and (ii).

BACKGROUND OF THE INVENTION

Polyols are valuable materials with uses such as PTA/PET, cold weather fluid, cosmetics and many others. Generating polyols from cellulose instead of olefins can be a more environmentally friendly and economically attractive process. Previously, polyols have been generated from polyhydroxy compounds, see WO 2010/060345, US 2004/0175806, and WO 2006/092085. Only recently, have polyols have been catalytically generated directly from cellulose in batch type processes. Catalytic conversion of cellulose into ethylene glycol over supported carbide catalysts was disclosed in Catalysis Today, 147, (2009) 77-85. US 2010/0256424, and US 2010/0255983 teach a method of preparing ethylene glycol from cellulose and a tungsten carbide catalyst to catalyze the reaction. Tungsten carbide catalysts have also been published as successful for batch-mode direct catalytic conversion of cellulose to ethylene glycol in Angew. Chem. Int. Ed 2008, 47, 8510-8513 and supporting information. A small amount of nickel was added to a tungsten carbide catalyst in Chem. Comm. 2010, 46, 862-864. Bimetallic catalysts have been disclosed in ChemSusChem, 2010, 3, 63-66.

However, there remains a need for a catalytic process for direct conversion of cellulose to polyol that is better suited for larger scale production or ongoing production. The continuous catalytic process for generating at least one polyol from a cellulose containing feedstock described herein addresses this need.

SUMMARY OF THE INVENTION

The invention relates to a continuous process for generating at least one polyol from a cellulose containing feedstock. The process involves, contacting, in a continuous manner, hydrogen, water, and a feedstock comprising cellulose, with a catalyst to generate an effluent stream comprising at least one polyol and recovering the polyol from the effluent stream. The hydrogen, water, and feedstock, are flowed in a continuous manner. The effluent stream is flowed in a continuous manner. The process is a catalytic process employing a catalyst consisting essentially of at least two active metal components selected from the group consisting of: (i) Mo, W, V, Ni, Co, Fe, Ta, Nb, Ti, Cr, Zr and combinations thereof wherein the metal is in the elemental state or the metal is a carbide compound, a nitride compound, or a phosphide compound; (ii) Pt, Pd, Ru, and combinations thereof wherein the metal is in the elemental state; and (iii) any combination of (i) and (ii).

In one embodiment, the contacting occurs in a reaction zone having at least a first input stream and a second input stream, the first input stream comprising at least the feedstock comprising cellulose and the second input stream comprising hydrogen. The first input stream may be pressurized prior to the reaction zone and the second input stream may be pressurized and heated prior to the reaction zone. The first input stream may be pressurized and heated to a temperature below the decomposition temperature of the cellulose prior to the reaction zone and the second input stream may be pressurized and heated prior to the reaction zone. The first input stream and the second input stream further comprise water.

In an embodiment of the invention, the polyol produced is at least ethylene glycol or propylene glycol. Co-products such as alcohols, organic acids, aldehydes, monosaccharides, polysaccharides, phenolic compounds, hydrocarbons, glycerol, depolymerized lignin, carbohydrates, and proteins may also be generated. In one embodiment, the feedstock may be treated prior to contacting with the catalyst by a technique such as sizing, drying, grinding, hot water treatment, steam treatment, hydrolysis, pyrolysis, thermal treatment, chemical treatment, biological treatment, catalytic treatment, or combinations thereof.

The feedstock may be continuously contacted with the catalyst in a system such as an ebullating catalyst bed system, an immobilized catalyst system having catalyst channels, an augured reaction system, or a slurry reactor system. When using a slurry reactor system, the temperature in the slurry reactor system may range from about 100° C. to about 350° C. and the hydrogen pressure may be greater than about 150 psig. In one embodiment, the temperature in the slurry reactor system may range from about 150° C. to about 350° C., in another embodiment the temperature in the slurry reactor system may range from about 200° C. to about 280° C. The feedstock may be continuously contacted with the catalyst in a slurry reactor system operated at a water to feedstock comprising cellulose weight ratio ranging from about 1 to about 100, a catalyst to feedstock comprising cellulose weight ratio of greater than about 0.005, a pH of less than about 10 and a residence time of greater than five minutes. In another embodiment, the catalyst to feedstock comprising cellulose weight ratio is greater than about 0.01.

The effluent stream from the reactor system may also contain catalyst, and the catalyst may be separated from the effluent stream using a technique such as direct filtration, settling followed by filtration, hydrocyclone, fractionation, centrifugation, the use of flocculants, and precipitation.

DETAILED DESCRIPTION OF THE INVENTION

Figure 1:
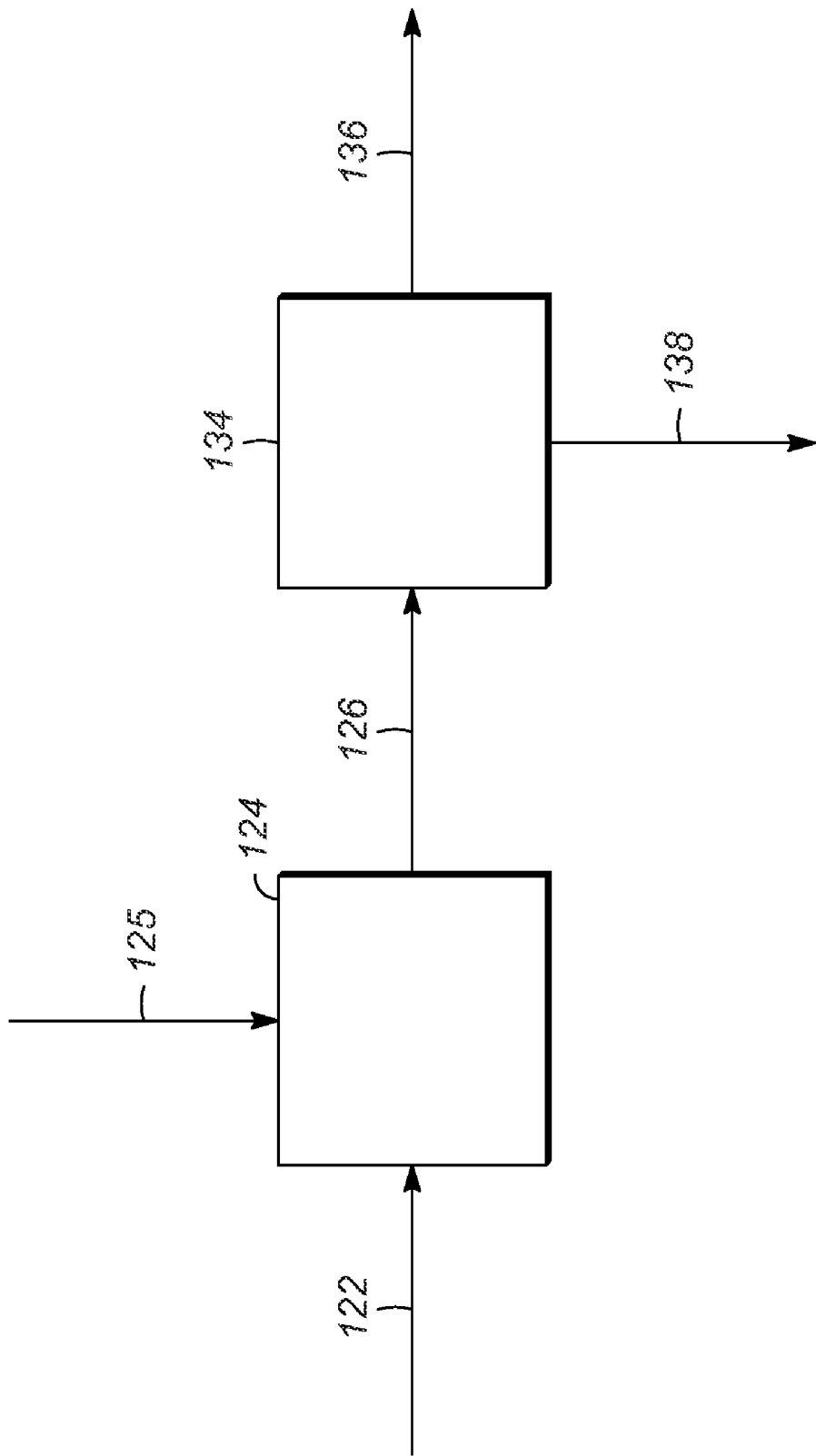
FIG. 1 is a basic diagram of the flow scheme of one embodiment of the invention. Equipment and processing steps not required to understand the invention are not depicted.

The invention involves a continuous process for generating at least one polyol from a feedstock comprising cellulose. The process involves continuous catalytic conversion of a flowing stream of cellulose to ethylene glycol or propylene glycol with high yield and high selectivity. The catalyst employed consists essentially of at least two active metal components selected from the group consisting of: (i) Mo, W, V, Ni, Co, Fe, Ta, Nb, Ti, Cr, Zr and combinations thereof wherein the metal is in the elemental state or the metal is a carbide compound, a nitride compound, or a phosphide compound; (ii) Pt, Pd, Ru, and combinations thereof wherein the metal is in the elemental state; and (iii) any combination of (i) and (ii).

In one embodiment, feedstock to the process comprises at least cellulose. Economic conversion of cellulose to useful products can be a sustainable process that reduces fossil energy consumption and does not directly compete with the human food supply. Cellulose is a large renewable resource having a variety of attractive sources, such as residue from agricultural production or waste from forestry or forest products. Since cellulose cannot be digested by humans, using cellulose as a feedstock does not take from our food supply. Furthermore, cellulose can be a low cost waste type feedstock material which is converted herein to high value products like polyols such as ethylene glycol and propylene glycol. In another embodiment, the feedstock to the process comprises at least hemicellulose.

The cellulose containing feedstock may be derived from sources such as biomass, pulp derived from biomass, waste material, recycled material. Examples include short rotation forestry, industrial wood waste, forest residue, agricultural residue, energy crops, industrial wastewater, municipal wastewater, paper, cardboard, fabrics and combinations thereof. Multiple materials may be used as co-feedstocks. With respect to biomass, the feedstock may be whole biomass including lignin and hemicellulose, treated biomass where the cellulose is at least partially depolymerized, or where the ligin, hemicellulose, or both have been at least partially removed from the whole biomass.

Unlike batch system operations, in a continuous process, the feedstock is continually being introduced into the reaction zone as a flowing stream and a product comprising a polyol is being continuously withdrawn. Materials must be capable of being transported from a source into the reaction zone, and products must be capable of being transported from the reaction zone. Depending upon the mode of operation, residual solids, if any, may be capable of being removed from the reaction zone.

A challenge in processing a cellulose containing feedstock in a pressurized hydrogen environment is that the feedstock is typically a solid. Therefore, pretreatment of the feedstock may be performed in order to facilitate the continuous transporting of the feedstock. Suitable pretreatment operations may include sizing, drying, grinding, hot water treatment, steam treatment, hydrolysis, pyrolysis, thermal treatment, chemical treatment, biological treatment, catalytic treatment, and combinations thereof. Sizing, grinding or drying may result in solid particles of a size that may be flowed or moved through a continuous process using a liquid or gas flow, or mechanical means. An example of a chemical treatment is mild acid hydrolysis, an example of catalytic treatment is catalytic hydrolysis, catalytic hydrogenation, or both, and an example of biological treatment is enzymatic hydrolysis. Hot water treatment, steam treatment, thermal treatment, chemical treatment, biological treatment, or catalytic treatment may result in lower molecular weight saccharides and depolymerized lignins that are more easily transported as compared to the untreated cellulose. Suitable pretreatment techniques are found in Ind. Eng. Chem. Res._DOI:10.1021/ie102505y, Publication Date (Web): Apr. 20, 2011 "Catalytic Hydrogenation of Corn Stalk to Ethylene Glycol and 1,2-Propylene Glycol" Jifeng Pang, Mingyuan Zheng, Aiqin Wang, and Tao Zhang. See also, US 2002/0059991.

Another challenge in processing a cellulose containing feedstock is that the cellulose is thermally sensitive. Exposure to excessive heating prior to contacting with the catalyst may result in undesired thermal reactions of the cellulose such as charring of the cellulose. In one embodiment of the invention, the feedstock comprising cellulose is provided to the reaction zone containing the catalyst in a separate input stream from the primary hydrogen stream. In this embodiment, the reaction zone has at least two input streams. The first input stream comprises at least the feedstock comprising cellulose, and the second input stream comprises at least hydrogen. Water may be present in the first input stream, the second input stream or in both input streams. Some hydrogen may also be present in the first input stream with the feedstock comprising cellulose. By separating the feedstock comprising cellulose and the hydrogen into two independent input streams, the hydrogen stream may be heated in excess of the reaction temperature without also heating the feedstock comprising cellulose to reaction temperature. The temperature of first input stream comprising at least the feedstock comprising cellulose may be controlled not to exceed the temperature of unwanted thermal side reactions. For example, the temperature of first input stream comprising at least the feedstock comprising cellulose may be controlled not to exceed the decomposition temperature of the cellulose or the charring temperature of the cellulose. The first input stream, the second input stream, or both may be pressurized to reaction pressure before being introduced to the reaction zone.

The feedstock comprising cellulose, after any pretreatment, is continuously introduced to a catalytic reaction zone as a flowing stream. Water and hydrogen, both reactants, are present in the reaction zone. As discussed above and depending upon the specific embodiment, at least a portion of the hydrogen may be introduced separately and independent from the feedstock comprising cellulose, or any combination of reactants, including feedstock comprising cellulose, may be combined and introduced to the reaction zone together. Because of the mixed phases likely to be present in the reaction zone specific types of systems are preferred. For example, suitable systems include ebullating catalyst bed systems, immobilized catalyst systems having catalyst channels, augured reaction systems, fluidized bed reactor systems, mechanically mixed reaction systems and slurry reactor systems, also known as a three phase bubble column reactor systems.

Furthermore, metallurgy of the reaction system is selected to be compatible with the reactants and the desired products within the range of operating conditions. Examples of suitable metallurgy for the reaction system include titanium, zirconium, stainless steel, carbon steel having hydrogen embrittlement resistant coating, carbon steel having corrosion resistant coating. In one embodiment, the metallurgy of the reaction system includes zirconium clad carbon steel.

Within the reaction zone and at operating conditions, the reactants proceed through catalytic conversion reactions to produce at least one polyol. Desired polyols include ethylene glycol and propylene glycol. Co-products may also be produced and include compounds such as alcohols, organic acids, aldehydes, monosaccharides, polysaccharides, phenolic compounds, hydrocarbons, glycerol, depolymerized lignin, carbohydrates, and proteins. The co-products may have value and may be recovered in addition to the product polyols. The reactions may proceed to completion, or some reactants and intermediates may remain in a mixture with the products. Intermediates, which are included herein as part of the co-products, may include compounds such as saccharides and hemicellulose. Unreacted hydrogen, water, and cellulose may also be present in the reaction zone effluent along with products and co-products. Unreacted material and or intermediates may be recovered and recycled to the reaction zone.

The reactions are catalytic reactions and the reaction zone comprises at least a catalyst consisting essentially of at least two active metal components selected from the group consisting of: (i) Mo, W, V, Ni, Co, Fe, Ta, Nb, Ti, Cr, Zr and combinations thereof wherein the metal is in the elemental state or the metal is a carbide compound, a nitride compound, or a phosphide compound; (ii) Pt, Pd, Ru, and combinations thereof wherein the metal is in the elemental state; and (iii) any combination of (i) and (ii). In some embodiments the catalyst may reside within the reaction zone, and in other embodiments the catalyst may continuously or intermittently pass through the reaction zone. Suitable catalytic systems include an ebullating catalyst bed system, an immobilized catalyst system having catalyst channels, an augured reaction system, fluidized bed reactor systems, mechanically mixed reaction systems and a slurry reactor system, also known as a three phase bubble column reactor system.

The catalyst consists essentially of at least two active metal components selected from the group consisting of: (i) Mo, W, V, Ni, Co, Fe, Ta, Nb, Ti, Cr, Zr and combinations thereof wherein the metal is in the elemental state or the metal is a carbide compound, a nitride compound, or a phosphide compound; (ii) Pt, Pd, Ru, and combinations thereof wherein the metal is in the elemental state; and (iii) any combination of (i) and (ii). Suitable examples of the catalyst are found, for example, in Angew. Chem. Int. Ed 2008, 47, 8510-8513 and supporting information and ChemSusChem 2010, 3, 63-66. The catalyst may further comprise a support which can be in the shape of a powder, or specific shapes such as spheres, extrudates, pills, pellets, tablets, irregularly shaped particles, monolithic structures, catalytically coated tubes, or catalytically coated heat exchanger surfaces. Examples of suitable supports include the refractory inorganic oxides including, but not limited to, silica, alumina, silica-alumina, titania, zirconia, magnesia, clays, zeolites, molecular sieves, etc. It should be pointed out that silica-alumina is not a mixture of silica and alumina but means an acidic and amorphous material that has been cogelled or coprecipitated. Carbon and activated carbon may also be employed as supports. Specific suitable supports include Carbon, Al2O3, ZrO2, SiO2, MgO, CexZrOy, TiO2, SiC. Of course mixtures of materials can be used as the support.

Details related to this type of catalyst may be found in US 2010/0255983 hereby incorporated be reference; US 2010/0256424 hereby incorporated be reference; U.S. Pat. No. 7,767,867, hereby incorporated by reference, WO2010/060345; Angew. Chem. Int. Ed 2008, 47, 8510-8513 and supporting information; Chem. Commun., 2010, 46, 6935-6937; Chem. Commun., 2010, 46, 862-864; Chin. J. Catal., 2006, 27(10): 899-903; ChemSusChem 2010, 3, 63-66; Catalysis Today 147 (2009) 77-85; and Apcseet UPC 2009 7$^{th}$ Asia Pacific Congress on Sustainable Energy and Environmental Technologies, "One-pot Conversion of Jerusalem Artichoke Tubers into Polyols."

In one embodiment of the invention, the catalytic reaction system employs a slurry reactor. Slurry reactors are also known as three phase bubble column reactors. Slurry reactor systems are known in the art and an example of a slurry reactor system is described in U.S. Pat. No. 5,616,304 and in Topical Report, Slurry Reactor Design Studies, DOE Project No. DE-AC22-89PC89867, Reactor Cost Comparisons, which may be found at the fischer-tropsch.org website under DOE report number 91005752.

The catalyst may be mixed with the feedstock comprising cellulose and water to form a slurry which is conducted to the slurry reactor. The reactions occur within the slurry reactor and the catalyst is transported with the effluent stream out of the reactor. The slurry reactor system may be operated at temperatures from about 100° C. to about 350° C. and the hydrogen pressure may be greater than about 150 psig. In one embodiment, the temperature in the slurry reactor system may range from about 150° C. to about 350° C., in another embodiment the temperature in the slurry reactor system may range from about 200° C. to about 280° C. The feedstock may be continuously contacted with the catalyst in a slurry reactor system operated at a water to feedstock comprising cellulose weight ratio ranging from about 1 to about 100, a catalyst to feedstock comprising cellulose weight ratio of greater than about 0.005, a pH of less than about 10 and a residence time of greater than 5 minutes. In another embodiment, the water to feedstock comprising cellulose weight ratio ranges from about 1 to about 20 and the catalyst to feedstock comprising cellulose weight ratio is greater than about 0.01. In yet another embodiment, the water to feedstock comprising cellulose weight ratio ranges from about 1 to about 5 and the catalyst to feedstock comprising cellulose weight ratio is greater than about 0.1.

In another embodiment the catalytic reaction system employs an ebullating bed reactor. Ebullating bed reactor systems are known in the art and an example of an ebullating bed reactor system is described in U.S. Pat. No. 6,436,279.

The effluent stream from the reaction zone contains at least the product polyol(s) and may also contain unreacted water, hydrogen, cellulose, byproducts such as phenolic compounds and glycerol, and intermediates such as depolymerized saccharides and lignins. Depending upon the catalytic reaction system used, the effluent stream may also contain catalyst particles. In some embodiments it may be advantageous to remove the catalyst particles from the effluent stream, either before or after and desired products or by-products are recovered. Catalyst particles may be removed from the effluent stream using one or more techniques such as direct filtration, settling followed by filtration, hydrocyclone, fractionation, centrifugation, the use of flocculants, precipitation, extraction, evaporation, or combinations thereof. In one embodiment, separated catalyst may be recycled to the reaction zone.

Turning to FIG. 1, catalyst, water, and feedstock comprising cellulose is conducted via stream 122 to reaction zone 124. The mixture in stream 122 has, for example, a water to feedstock comprising cellulose weight ratio of about 5 and a catalyst to feedstock comprising cellulose weight ratio of about 0.05. At least hydrogen is conducted via stream 125 to reaction zone 124. Reaction zone 124 is operated, for example, at a temperature of about 250° C. a hydrogen pressure of about 1200 psig, a pH of about 7 and a residence time of about 8 minutes. Prior to introduction into reaction zone 124, the catalyst, water, and feedstock comprising cellulose in stream 122 and the hydrogen in stream 125 are brought to a pressure of about 1800 psig to be at about the same pressure as reaction zone 124. However, only stream 125 comprising at least hydrogen is raised to at least 250° C. to be at a temperature greater than or equal to the temperature in reaction zone 124. The mixture in stream 122 which contains at least the cellulose is temperature controlled to remain at a temperature lower than the decomposition or charring temperature of the cellulose. In reaction zone 124, the cellulose is catalytically converted into at least ethylene glycol or propylene glycol. Reaction zone effluent 126 contains at least the product ethylene glycol or propylene glycol. Reaction zone effluent 126 may also contain alcohols, organic acids, aldehydes, monosaccharides, polysaccharides, phenolic compounds, hydrocarbons, glycerol, depolymerized lignin, carbohydrates, and proteins. Reaction zone effluent 126 is conducted to product recovery zone 134 where the desired glycol products are separated and recovered in steam 136. Remaining components of reaction zone effluent 126 are removed from product recovery zone 134 in stream 138.

Figure 2:
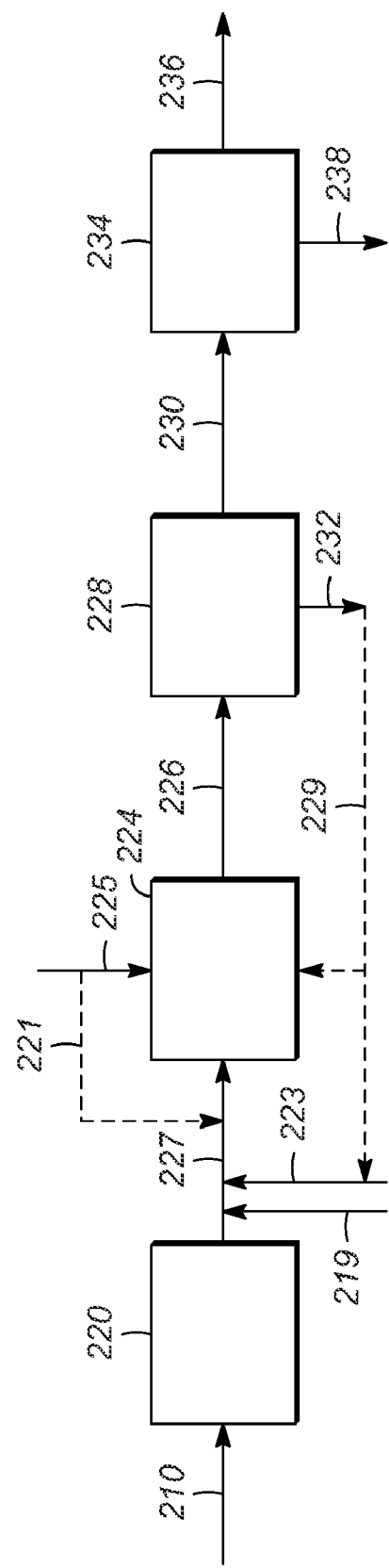
FIG. 2 is a basic diagram of the flow scheme of another embodiment of the invention showing an optional pretreatment zone and an optional catalyst separation zone with optional catalyst recycle. Equipment and processing steps not required to understand the invention are not depicted.

Turning to FIG. 2, water and feedstock comprising cellulose 210 is introduced to pretreatment unit 220 where the cellulose is ground to a particle size that is small enough to be pumped as a slurry with the water using conventional equipment. The pretreated feedstock is combined with water in line 219 and catalyst in line 223 and combined stream 227 is conducted to reaction zone 224. The combined stream 227 has, for example, a water to feedstock comprising cellulose weight ratio of about 20 and a catalyst to feedstock comprising cellulose weight ratio of about 0.1. At least hydrogen is conducted via stream 225 to reaction zone 224. Some hydrogen may be combined with stream 227 prior to reaction zone 224 as shown by optional dotted line 221. Reaction zone 224 is operated, for example, at a temperature of about 250° C. a hydrogen pressure of about 1200 psig, a pH of about 7 and a residence time of about 8 minutes. Prior to introduction into reaction zone 224, the catalyst, water, and pretreated feedstock comprising cellulose in stream 227 and the hydrogen in stream 225 are brought to a pressure of about 1800 psig to be at about the same temperature as reaction zone 224. However, only stream 225 comprising at least hydrogen is raised to, for example, at least 250° C. to be at a temperature greater than or equal to the temperature of reaction zone 224. The mixture in stream 227 which contains at least the cellulose is temperature controlled to remain at a temperature lower than the decomposition or charring temperature of the cellulose. In reaction zone 224, the cellulose is catalytically converted into at least ethylene glycol or polyethylene glycol.

Reaction zone effluent 226 contains at least the product ethylene glycol or propylene glycol and catalyst. Reaction zone effluent 226 may also contain alcohols, organic acids, aldehydes, monosaccharides, polysaccharides, phenolic compounds, hydrocarbons, glycerol, depolymerized lignin, carbohydrates, and proteins. Reaction zone effluent 226 is conducted to optional catalyst recovery zone 228 where the catalyst is separated from reaction zone effluent 226 and removed in line 232. Catalyst in line 232 may optionally be recycled to combine with line 223 or to reaction zone 224 as shown by optional dotted line 229. The catalyst-depleted reaction zone effluent 230 is conducted to product recovery zone 234 where the desired glycol products are separated and recovered in steam 236. Remaining components of catalyst-depleted reaction zone effluent 230 are removed from product recovery zone 234 in stream 238.

The invention claimed is:

1. A process for generating at least one polyol from a feedstock comprising:
   contacting, in a continuous manner, hydrogen, water, and a feedstock comprising cellulose, with a catalyst to generate an effluent stream comprising at least one polyol; wherein the hydrogen, water, and feedstock comprising cellulose are flowing in a continuous manner; wherein the catalyst consists essentially of at least two active metal components selected from the group consisting of:
   i.) Mo, W, V, Ni, Co, Fe, Ta, Nb, Ti, Cr, Zr and combinations thereof wherein the metal is in the elemental state or the metal is a carbide compound, a nitride compound, or a phosphide compound;
   ii.) Pt, Pd, Ru, and combinations thereof wherein the metal is in the elemental state; and
   iii.) any combination of i.) and ii.);
   recovering the polyol from the effluent stream; and
   wherein the contacting occurs in a reaction zone comprising at least a first input stream and a second input stream, the first input stream comprising at least the flowing feedstock comprising cellulose and the second input stream comprising flowing hydrogen.

2. The process of claim 1 wherein the first input stream is pressurized prior to the reaction zone and the second input stream is pressurized and heated prior to the reaction zone.

3. The process of claim 1 wherein the first input stream is pressurized and heated to a temperature below the decomposition temperature of the cellulose prior to the reaction zone and the second input stream is pressurized and heated prior to the reaction zone.

4. The process of claim 1 wherein the first input stream and the second input stream further comprise water.

5. The process of claim 1 wherein the catalyst further contains a support.

6. The process of claim 5 wherein the support is selected from Carbon, $Al_2O_3$, $ZrO_2$, $SiO_2$, MgO, CexZrOy, $TiO_2$, SiC, and combinations thereof.

7. The process of claim 1 wherein the feedstock comprising cellulose is selected from the group consisting of biomass, pulp derived from biomass, waste material, recycled material, and combinations thereof.

8. The process of claim 1 wherein the feedstock comprising cellulose is selected from the group consisting of short rotation forestry, industrial wood waste, forest residue, agricultural residue, energy crops, industrial wastewater, municipal wastewater, paper, cardboard, fabrics and combinations thereof.

9. The process of claim 1 wherein the polyol is selected from the group consisting of ethylene glycol and propylene glycol.

10. The process of claim 1 wherein the effluent stream further comprises at least one co-product selected from the group consisting of alcohols, organic acids, aldehydes, monosaccharides, polysaccharides, phenolic compounds, hydrocarbons, glycerol, depolymerized lignin, carbohydrates, and proteins.

11. The process of claim 1 further comprising preparing the feedstock comprising cellulose prior to contacting with the catalyst by a technique selected from the group consisting of sizing, drying, grinding, hot water treatment, steam treatment, hydrolysis, pyrolysis, thermal treatment, chemical treatment, biological treatment, catalytic treatment, and combinations thereof.

12. The process of claim 11 wherein the chemical treatment comprises acid catalyzed hydrolysis or base catalyzed hydrolysis, wherein the catalytic treatment comprises depolymerization, catalytic hydrogenation, or both, and wherein the biological treatment comprises enzymatic hydrolysis.

13. The process of claim 1 wherein the flowing hydrogen, flowing water, and flowing feedstock is contacted with the catalyst in a reactor having metallurgy comprising a component selected from the group consisting of titanium, zirconium, stainless steel, carbon steel having hydrogen embrittlement resistant coating, carbon steel having corrosion resistant coating.

14. The process of claim 1 wherein the hydrogen, water, and feedstock is contacted with the catalyst in a system selected from the group consisting of an ebullating catalyst bed system, an immobilized catalyst reaction system having catalyst channels, an augured reaction system, a fluidized bed reaction system, a mechanically mixed reaction system, and a slurry reactor system.

15. The process of claim 1 wherein the flowing hydrogen, water, and feedstock are contacted with the catalyst in a slurry reactor system operated at a temperature ranging from about 100° C. to about 350° C. and a hydrogen pressure greater than about 150 psig.

16. The process of claim 1 wherein the hydrogen, water, and feedstock are contacted with the catalyst in a reaction zone operated at conditions sufficient to maintain at least a portion of the water in the liquid phase.

17. The process of claim 1 wherein the hydrogen, water, and feedstock are continuously contacted with the catalyst in a slurry reactor system operated at a water to feedstock comprising cellulose weight ratio ranging from about 1 to about 100, a catalyst to feedstock comprising cellulose weight ratio of greater than about 0.005, a pH of less than about 10 and a residence time of greater than 5 minutes.

18. The process of claim 17 wherein the effluent stream further comprises catalyst, said process further comprising separating at least the catalyst from the effluent stream using a technique selected from the group consisting of direct filtration, settling followed by filtration, hydrocyclone, fractionation, centrifugation, the use of flocculants, precipitation, liquid extraction, evaporation, and combinations thereof.

19. The process of claim 18 wherein the hydrogen, water, and feedstock are continuously contacted with the catalyst in a reactor, said process further comprising recycling the separated catalyst to the reactor.

20. A process for generating at least one polyol from a feedstock comprising:
contacting, in a continuous manner, hydrogen, water, and a feedstock comprising cellulose, with a catalyst to generate an effluent stream comprising at least one polyol; wherein the hydrogen, water, and feedstock comprising cellulose are flowing in a continuous manner; wherein the catalyst consists essentially of at least two active metal components selected from the group consisting of:
i.) Mo, W, V, Ni, Co, Fe, Ta, Nb, Ti, Cr, Zr and combinations thereof wherein the metal is in the elemental state or the metal is a carbide compound, a nitride compound, or a phosphide compound;
ii.) Pt, Pd, Ru, and combinations thereof wherein the metal is in the elemental state; and
iii.) any combination of i.) and ii.);
recovering the polyol from the effluent stream; and wherein the feedstock is prepared prior to contacting with the catalyst by a technique selected from the group consisting of sizing, drying, grinding, hot water treatment, steam treatment, hydrolysis, pyrolysis, thermal treatment, chemical treatment, biological treatment, catalytic treatment, and combinations thereof, wherein the chemical treatment comprises acid catalyzed hydrolysis or base catalyzed hydrolysis, wherein the catalytic treatment comprises depolymerization, catalytic hydrogenation, or both, and wherein the biological treatment comprises enzymatic hydrolysis.

21. A process for generating at least one polyol from a feedstock comprising:
contacting, in a continuous manner, hydrogen, water, and a feedstock comprising cellulose, with a catalyst to generate an effluent stream comprising at least one polyol; wherein the hydrogen, water, and feedstock comprising cellulose are flowing in a continuous manner; wherein the catalyst consists essentially of at least two active metal components selected from the group consisting of:
i.) Mo, W, V, Ni, Co, Fe, Ta, Nb, Ti, Cr, Zr and combinations thereof wherein the metal is in the elemental state or the metal is a carbide compound, a nitride compound, or a phosphide compound;
ii.) Pt, Pd, Ru, and combinations thereof wherein the metal is in the elemental state; and
iii.) any combination of i.) and ii.);
recovering the polyol from the effluent stream; and wherein the flowing hydrogen, flowing water, and flowing feedstock is contacted with the catalyst in a reactor having metallurgy comprising a component selected from the group consisting of titanium, zirconium, stainless steel, carbon steel having hydrogen embrittlement resistant coating, carbon steel having corrosion resistant coating.

22. A process for generating at least one polyol from a feedstock comprising:
contacting, in a continuous manner, hydrogen, water, and a feedstock comprising cellulose, with a catalyst to generate an effluent stream comprising at least one polyol; wherein the hydrogen, water, and feedstock comprising cellulose are flowing in a continuous manner; wherein the catalyst consists essentially of at least two active metal components selected from the group consisting of:
i.) Mo, W, V, Ni, Co, Fe, Ta, Nb, Ti, Cr, Zr and combinations thereof wherein the metal is in the elemental state or the metal is a carbide compound, a nitride compound, or a phosphide compound;
ii.) Pt, Pd, Ru, and combinations thereof wherein the metal is in the elemental state; and
iii.) any combination of i.) and ii.);
recovering the polyol from the effluent stream; and wherein the hydrogen, water, and feedstock is contacted with the catalyst in a system selected from the group consisting of an ebullating catalyst bed system, an immobilized catalyst reaction system having catalyst channels, an augured reaction system, a fluidized bed reaction system, a mechanically mixed reaction system, and a slurry reactor system.

23. A process for generating at least one polyol from a feedstock comprising:
contacting, in a continuous manner, hydrogen, water, and a feedstock comprising cellulose, with a catalyst to generate an effluent stream comprising at least one polyol; wherein the hydrogen, water, and feedstock comprising cellulose are flowing in a continuous manner; wherein the catalyst consists essentially of at least two active metal components selected from the group consisting of:
i.) Mo, W, V, Ni, Co, Fe, Ta, Nb, Ti, Cr, Zr and combinations thereof wherein the metal is in the elemental state or the metal is a carbide compound, a nitride compound, or a phosphide compound;
ii.) Pt, Pd, Ru, and combinations thereof wherein the metal is in the elemental state; and
iii.) any combination of i.) and ii.);
recovering the polyol from the effluent stream; and wherein the hydrogen, water, and feedstock are continuously contacted with the catalyst in a slurry reactor system operated at a water to feedstock comprising cellulose weight ratio ranging from about 1 to about 100, a catalyst to feedstock comprising cellulose weight ratio of greater than about 0.005, a pH of less than about 10 and a residence time of greater than 5 minutes.

24. The process of claim 23 wherein the effluent stream further comprises catalyst, said process further comprising separating at least the catalyst from the effluent stream using a technique selected from the group consisting of direct filtration, settling followed by filtration, hydrocyclone, fractionation, centrifugation, the use of flocculants, precipitation, liquid extraction, evaporation, and combinations thereof.

25. The process of claim 23 wherein the hydrogen, water, and feedstock are continuously contacted with the catalyst in a reactor, said process further comprising recycling the separated catalyst to the reactor.

* * * * *